(12) United States Patent
Prestidge et al.

(10) Patent No.: US 6,712,790 B1
(45) Date of Patent: Mar. 30, 2004

(54) PARENTERAL CATHETER APPARATUS

(76) Inventors: Dean Brian Prestidge, 7 Key West Drive, Mullalloo, Western Australia 6027 (AU); Maxwell Edmund Whisson, 5/70 Subiaco Road, Subiaco, Western Australia 6008 (AU)

( * ) Notice: Subject to any disclaimer, the term of this patent is extended or adjusted under 35 U.S.C. 154(b) by 0 days.

(21) Appl. No.: 09/869,655
(22) PCT Filed: Dec. 24, 1999
(86) PCT No.: PCT/AU99/01168
§ 371 (c)(1), (2), (4) Date: Jun. 28, 2001
(87) PCT Pub. No.: WO00/40287
PCT Pub. Date: Jul. 13, 2000

(30) Foreign Application Priority Data

Dec. 31, 1998 (AU) .............................. PP7989

(51) Int. Cl.[7] .............................. A61M 5/178
(52) U.S. Cl. .................. 604/164.06; 604/164.01; 604/177; 604/171
(58) Field of Search ................. 604/158, 164, 604/164.01, 171, 165.01, 165.02, 165.03, 177, 164.06

(56) References Cited

U.S. PATENT DOCUMENTS

| 4,160,450 A | * | 7/1979 | Doherty .................. 128/214.4 |
| 4,955,863 A | * | 9/1990 | Walker et al. ............... 604/165 |
| 5,462,533 A | * | 10/1995 | Daugherty ................... 604/164 |
| 5,498,241 A | * | 3/1996 | Fabozzi ...................... 604/177 |
| 5,569,288 A | * | 10/1996 | Yoon .......................... 604/185 |
| 5,573,510 A | * | 11/1996 | Isaacson ...................... 604/158 |
| 5,573,512 A | * | 11/1996 | van den Haak ............. 604/171 |
| 5,676,656 A | * | 10/1997 | Brimhall ..................... 604/165 |
| 5,697,914 A | * | 12/1997 | Brimhall ..................... 604/177 |
| 5,779,679 A | | 7/1998 | Shaw |
| 5,893,845 A | * | 4/1999 | Newby et al. ............... 604/198 |
| 5,906,594 A | * | 5/1999 | Scarfone et al. ............ 604/165 |

FOREIGN PATENT DOCUMENTS

WO  98/30259  7/1998

* cited by examiner

Primary Examiner—Henry Bennett
Assistant Examiner—Camtu Nguyen
(74) Attorney, Agent, or Firm—Bachman & LaPointe, P.C.

(57) ABSTRACT

A parenteral catheter apparatus (40) comprises a catheter (18) enclosing a needle (20). The needle (20) and catheter (18) have a first position in which a sharp point (22) of the needle (20) extends from the catheter (18) and a second position in which the sharp point (22) is enclosed within a housing (12). Further, a tubular member (15) is connected to the needle (20). The tubular member (15) has a connection means (17) for connection to a fluid container. Thus, fluid can flow through the tube (15) and the needle (20) and in the reverse direction The needle (20) remains in a fluid pathway of the apparatus at all times.

11 Claims, 12 Drawing Sheets

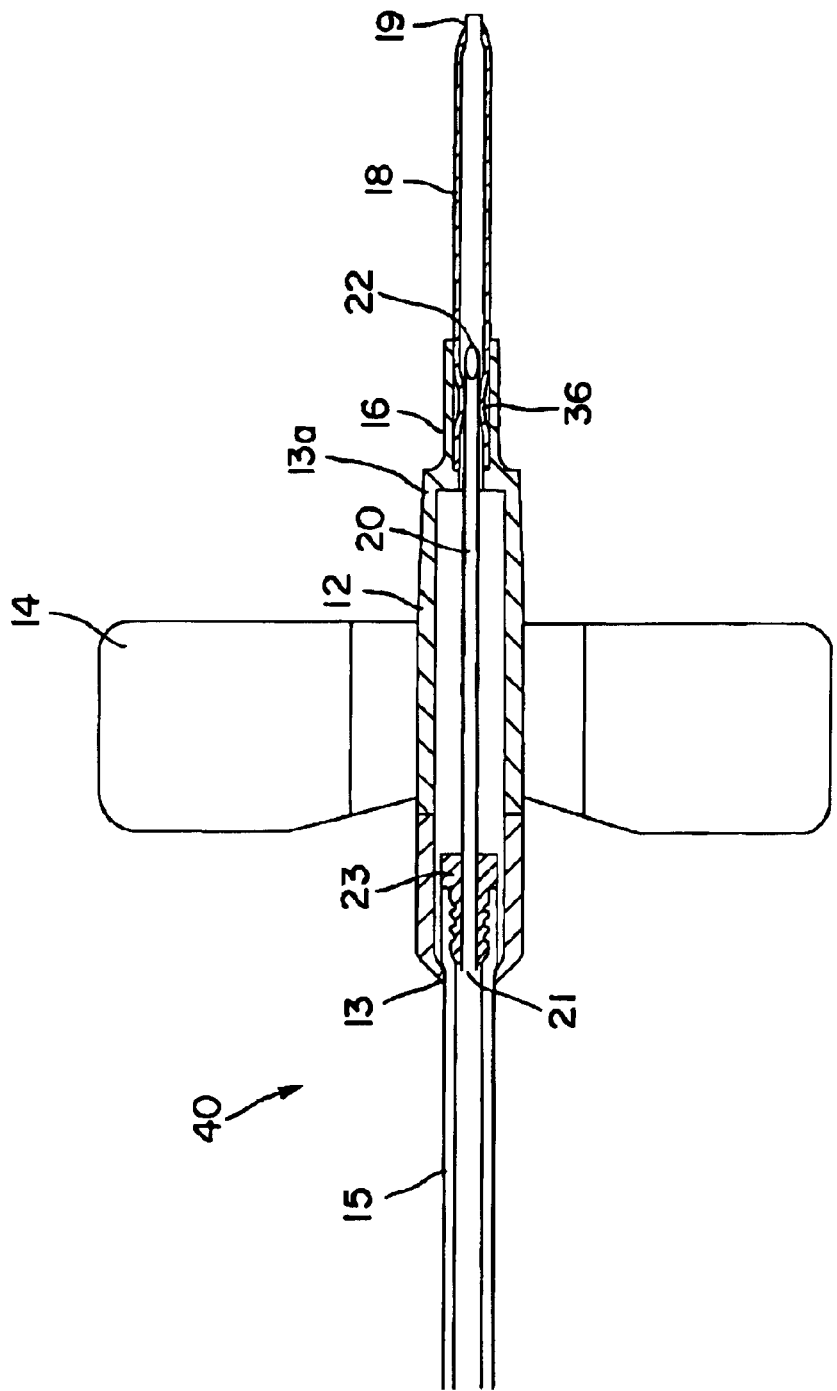

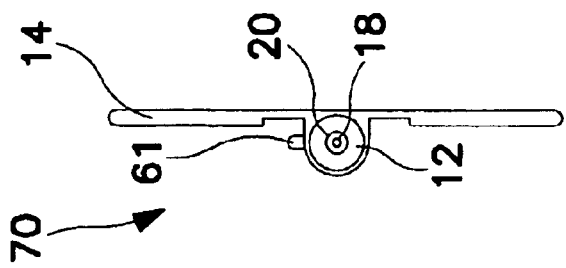
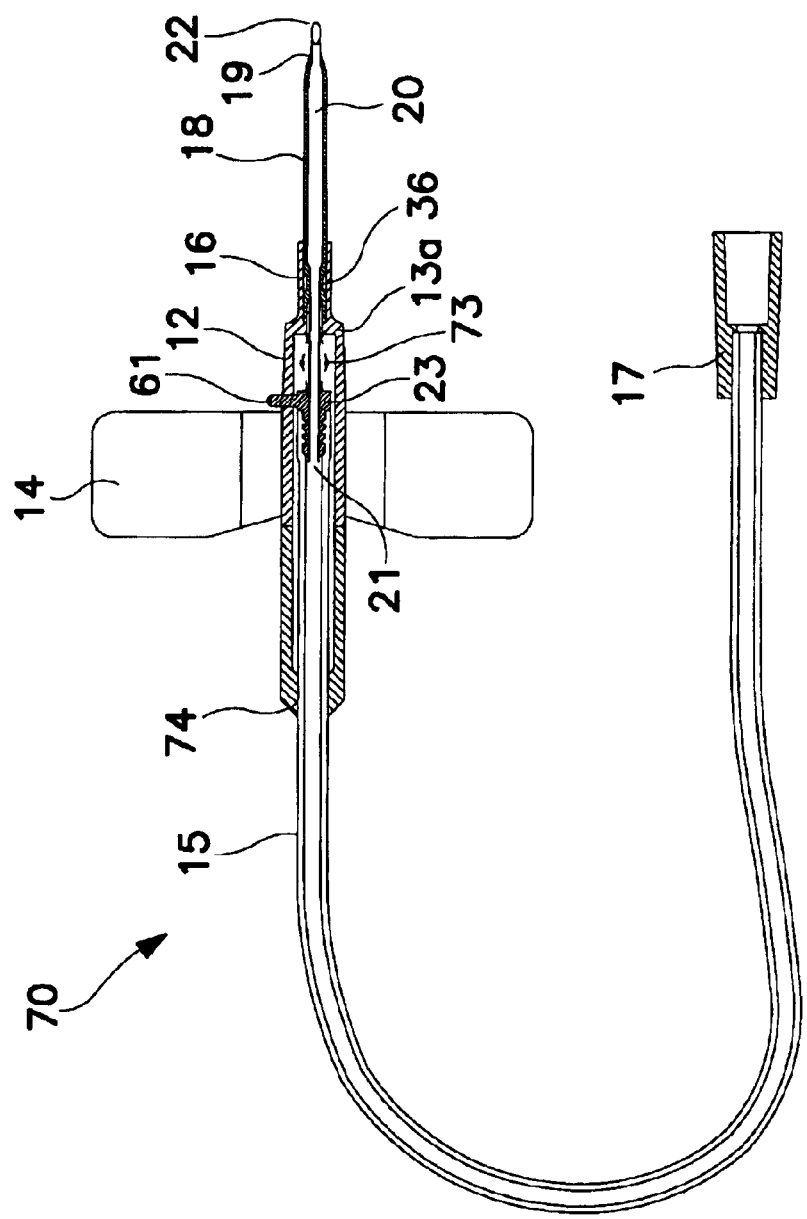

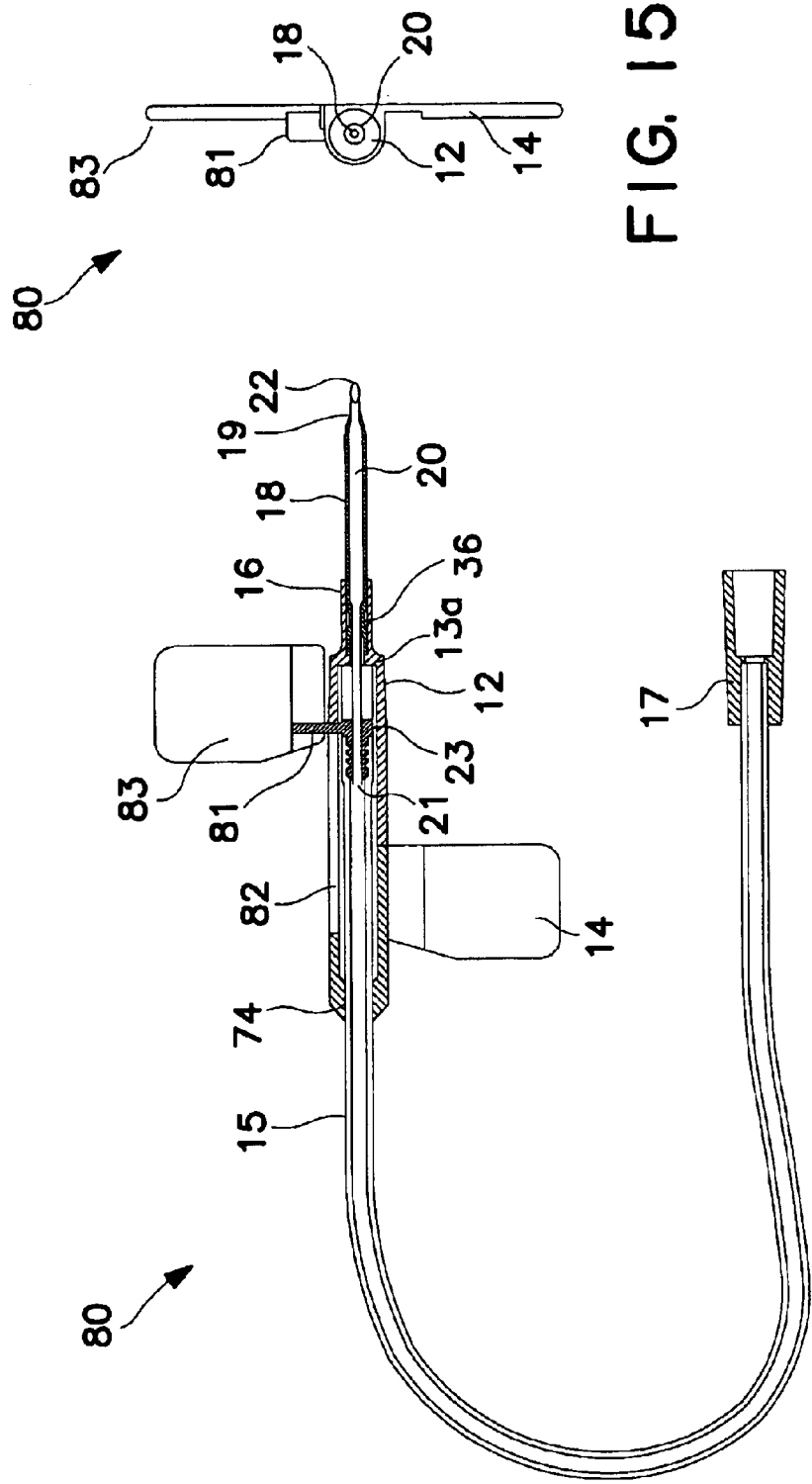

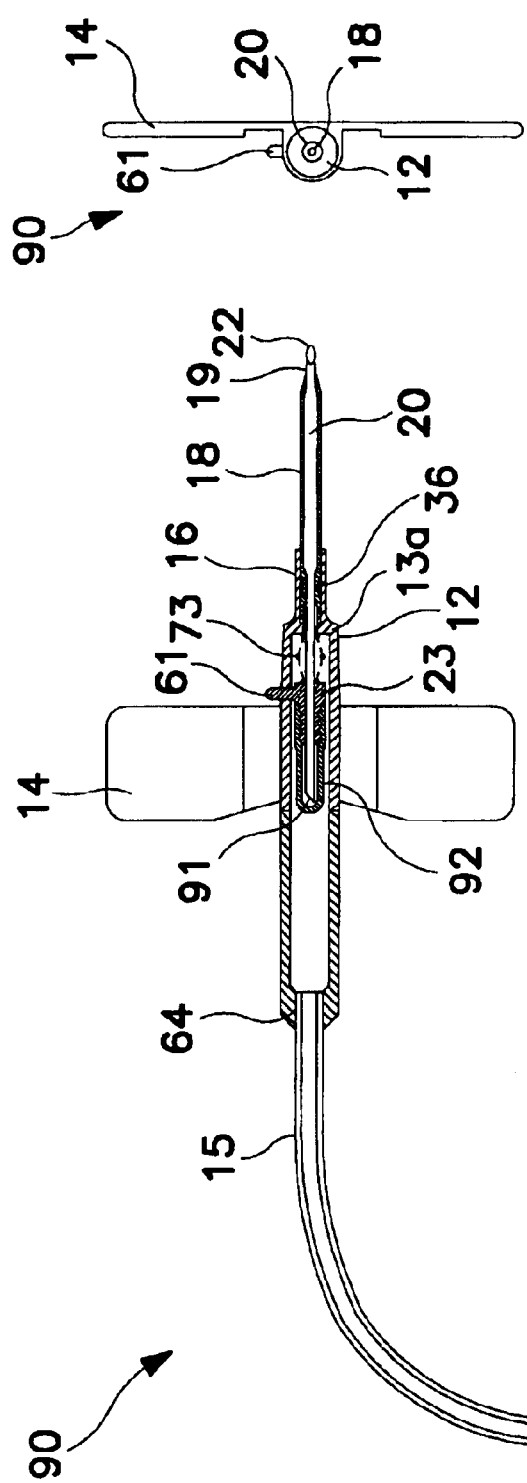

PARENTERAL CATHETER APPARATUS

FIELD OF THE INVENTION

The present invention relates to a parenteral catheter apparatus

PRIOR ART

Injection devices which use a sharp needle to enter human tissue are now widely recognized as being hazardous to users and other individuals because the sharp point, contaminated by its exposure to the tissue of the first person may penetrate the skin of a second person and in doing so may carry micro-organisms from the patient on whom the injection device was first used into the tissue of a second person. Such transmission may result in the development of disease in the second person and when the puncture of the skin is accidental it is referred to as "needlestick injury" or "needleprick injury".

Some clinical procedures require that a soft flexible tube, frequently called a catheter, is introduced into a tube or blood vessel such as a vein or artery or a parenteral fluid passage such as within the nervous system in the living body. This procedure is required, for example, to draw blood from a vein of a blood donor or from a patient for pathology testing; to infuse parenteral fluid nutrition or medication, especially when large volumes, for example several litres, are required to be infused over many hours; and also to enter the veins of patients who cannot be relied on to remain immobile during the procedure, in which situation a flexible catheter, rather than a stiff steel needle, greatly facilitates the procedure and is much less likely to damage the wall of the blood vessel.

The catheter is soft and flexible it cannot be used to penetrate the skin or the wall of the blood vessel and this is generally achieved by inserting a stiff sharp needle, which is generally called a trocar, through the lumen of the catheter so that the sharp tip of the trocar protrudes slightly during the procedure and pierces the tissue, splinting and carrying the catheter into the blood vessel. Having achieved this the operator then withdraws the trocar and discards it in a thick-walled container called a "sharps container". During this procedure strict rules are followed in order to avoid needlestrick injury, with the risk of nosocomial disease transmission, but the risk is high. There are other disadvantages associated with this arrangement. Withdrawal of the trocar leaves the catheter or a container which may be attached to it, open, so that for example blood. can leak from a vein. To prevent this the operator quickly attaches a tube or syringe or other container to the open end of the container attached to the open catheter. Another disadvantage is that confirmation that a bodily fluid has been entered, by observation of flow of that fluid, called flashback, along the lumen of the catheter, can only be achieved by first removing the trocar.

If the catheter is in fact in the chosen location the trocar may have to be re-introduced and the tissue further penetrated, with consequent danger of the introduction of infective particles into the living body. Ingenious techniques have been devised in attempts to overcome these problems. There are several topological problems in achieving this. If The trocar is to be moved to a position within the device where there is no danger of contacting infectious agents or of causing a needlestick injury then some handle means must be provided which is accessible from outside the device but acts on the trocar within the device. This may be in the form of a thread which must pass through a wall of the device. To achieve observable flashback, a very fine tube or channel may be formed in the trocar, but because of the topological restraints this channel must be too fine to be useful in delivering or drawing out fluid and, like other trocars, must be removed from the fluid channel in order to bring the device into the useable state.

It is an object of the present invention to alleviate these problems at least in part.

BRIEF DESCRIPTION OF THE INVENTION

In accordance with one aspect of the present invention there is provided a parenteral catheter apparatus characterised in that it comprises a thin walled catheter having a free end, the catheter closely enclosing a tubular needle having a sharp point, the catheter being mounted to a housing having a first end and a second end, the needle and catheter being longitudinally moveable relative to one another between a first position at which the needle extends from the catheter so that the sharp point is exposed and a second position at which the sharp point is within the catheter, the needle remaining in a fluid pathway of the parenteral catheter apparatus at all times between the first and second positions, the sharp point of the needle being arranged to pierce tissue when the catheter and the needle are in their relative first position, and the needle being connected or arranged to be connected to a tubular member arranged to be connected to a fluid container so that, in use, when the catheter and the needle are in their relative second position, parenteral fluid flows in order from the container into the tubular member, into the needle and into the catheter or fluid flows in the reverse direction in order into the catheter, into the needle, into the tubular member and then into the container.

BRIEF DESCRIPTION OF THE DRAWINGS

The present invention will now be described, by way of example, with reference to the accompanying drawings, in which:

FIG. 2 is a view similar to FIG. 1 in which the parenteral catheter apparatus is in a second position suitable for the transfer of parenteral fluid into or from a living body or for safe disposal after use.

FIG. 10 is a longitudinal sectional view of a fourth embodiment of the parenteral catheter apparatus of the present invention with the needle apparatus in a first position;

FIG. 12 is a schematic transverse view of the parenteral catheter apparatus shown in FIGS. 10 and 11;

FIG. 13 is a longitudinal sectional view of a fifth embodiment of the parenteral catheter apparatus of the present invention with the needle apparatus in a first position;

FIG. 15 is a schematic transverse view of the fifth embodiment of the parenteral catheter apparatus of FIGS. 13 and 14;

FIG. 16 is a longitudinal sectional view of a sixth embodiment of the parenteral catheter apparatus of the present invention with a needle apparatus in a first position;

FIG. 18 is a schematic transverse view of part of the sixth embodiment of the parenteral catheter apparatus of FIGS. 16 and 17.

The parenteral catheter apparatus of the present invention will now be described in greater detail by reference to the Figures, in which the same numbers are used to refer to similar parts throughout.

Figure 3:
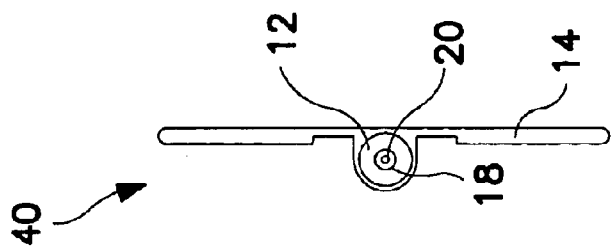
FIG. 3 is a transverse view of the parenteral catheter apparatus of FIGS. 1 and 2.

In the description which follows "needle" means a thin walled stiff tube or C section such as a steel tube, sharpened at least at one end. "Needle apparatus" means the needle together with a needle hub and parenteral fluid tube end which may be attached to it to ensure confinement of a fluid path as desired for the functional action described. "Catheter" means a thin walled flexible tube, attached at one end and free or capable of being made free at the other end and preferably formed of inert plastic elastomer which can be fitted closely but slidingly to the outer wall of the chosen needle. The dimensions and mechanical properties of the needle and catheter may be optimised to suit particular applications and the diameter, wall thickness, hardness and stiffness may if desired be varied along the length. Both catheter and needle or catheter or needle may be formed of composite materials to suit particular applications.

It may be possible to move the needle from a first position to a second position and to deliver parenteral fluid to or from the catheter/needle complex in a number of ways and some of the preferred arrangements are shown in the drawings.

Figure 1:
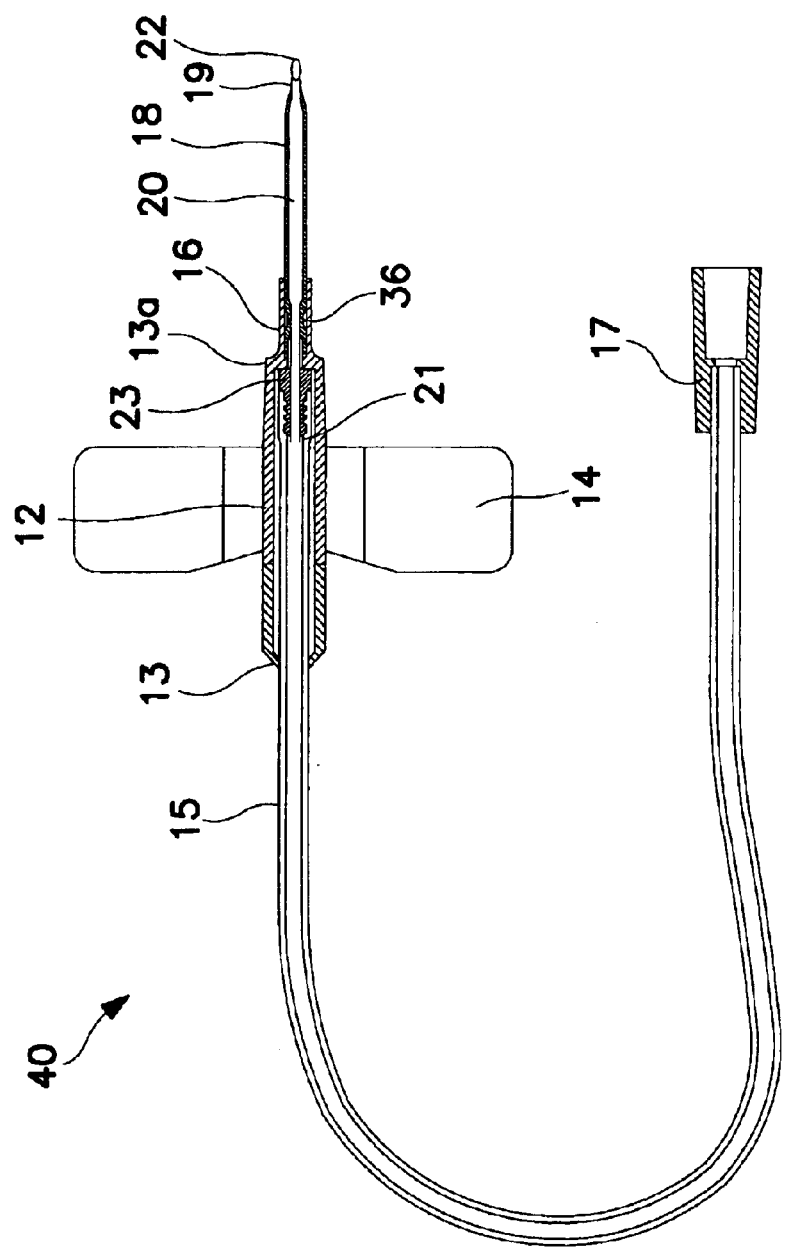
FIG. 1 is a longitudinal sectional view of a first embodiment of a parenteral catheter apparatus in accordance with the present invention in a first position ready for use to pierce body tissue and transfer fluid to or from the tissue.

FIGS. 1, 2 and 3 of the drawings illustrate a parenteral catheter apparatus 40 having a substantially tubular housing 12 with, fixed or formed upon it, one or more wing shaped projections 14 to aid manipulations. The housing 12 has a second end 13 which is inwardly tapered. Further, the housing 12 is extended at a first end 13a to form a tubular boss 16 adapted to firmly and sealingly attach a catheter 18 having an outer end 19. A thin walled tubular needle 20, sharpened at an outer end 22 is fitted sealingly within the catheter 18 such that in a first position as shown in FIG. 1 the end 22 projects slightly beyond the end 19 of the catheter 18. The catheter 18 sealing engages with the needle 20 at 36 by being inturned slightly. The needle 20 also has an inner end 21. A hub 23 is firmly and sealingly fixed to the inner end 21 of needle 20. A flexible tube 15 suitable for the transfer of parenteral fluid is fixed sealingly to the hub 23. As shown in FIG. 1, the tube 15 terminates in a luer or similar connector 17. The apparatus can slide axially and freely within the housing 12, with the exception that the tapered end 13 of housing 12 forms a constriction which engages with the tube 15 and which greatly restricts movement of the tube 15 from the second position (FIG. 2) toward the first position. Thus, once the needle 20 has been moved from the first position to the second position it will not readily move back to the first position. In order to move the needle 20 from the first to the second position after body tissue has been pierced, the wings 14 may be fixed, such as by taping to the skin or holding with an operator's thumb and forefinger. Traction may then be applied to the parenteral fluid tube 15. This action would normally be performed immediately after the operator confirms that a vein has been entered by seeing blood appear in the tube 15. A transparent housing 12 may be preferred so that the first drop of blood exiting from a vein can be seen emerging from the needle end 21. Alternatively the housing 12 may have a viewing port formed as a hole in a wall in the region of the needle end 21. In FIG. 2, it can be seen that the end 22 is disposed within the tubular boss 16 of the housing 12 when in the second position described above.

Figure 6:
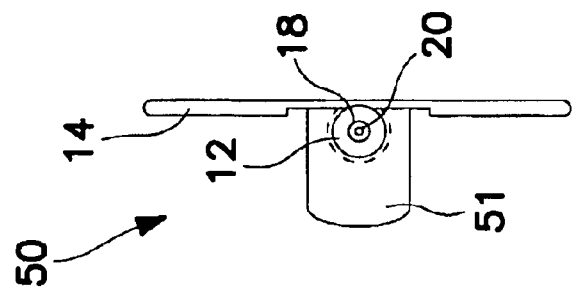
FIG. 6 is a transverse view of the parenteral catheter apparatus of FIG. 4.
Figure 4:
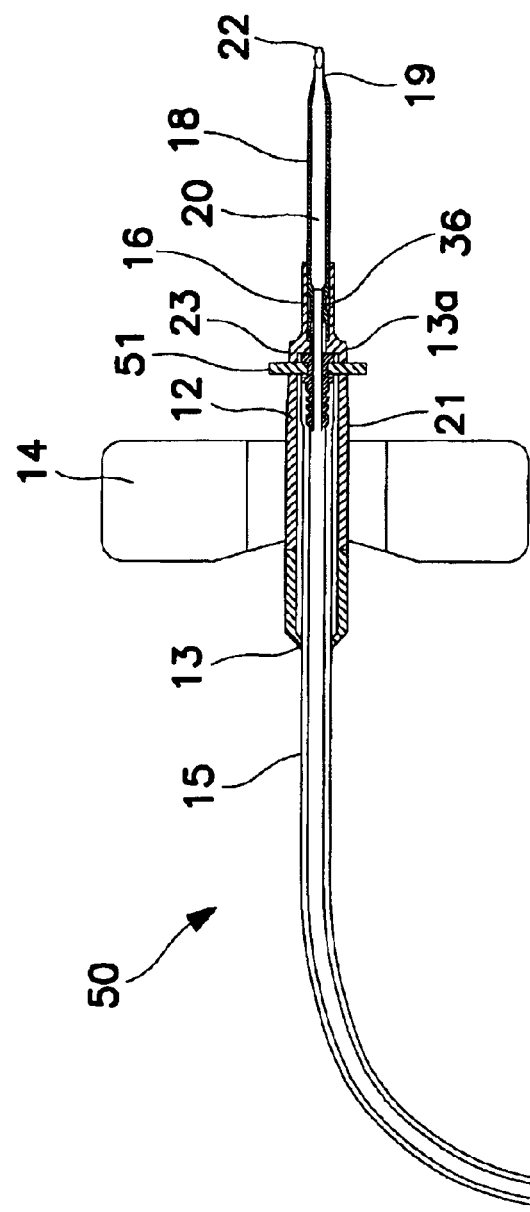
FIG. 4 is a longitudinal sectional view of a second embodiment of the parenteral catheter apparatus of the present invention with a needle apparatus in a first position suitable for penetrating living tissue or briefly transferring parenteral fluid.
Figure 5:
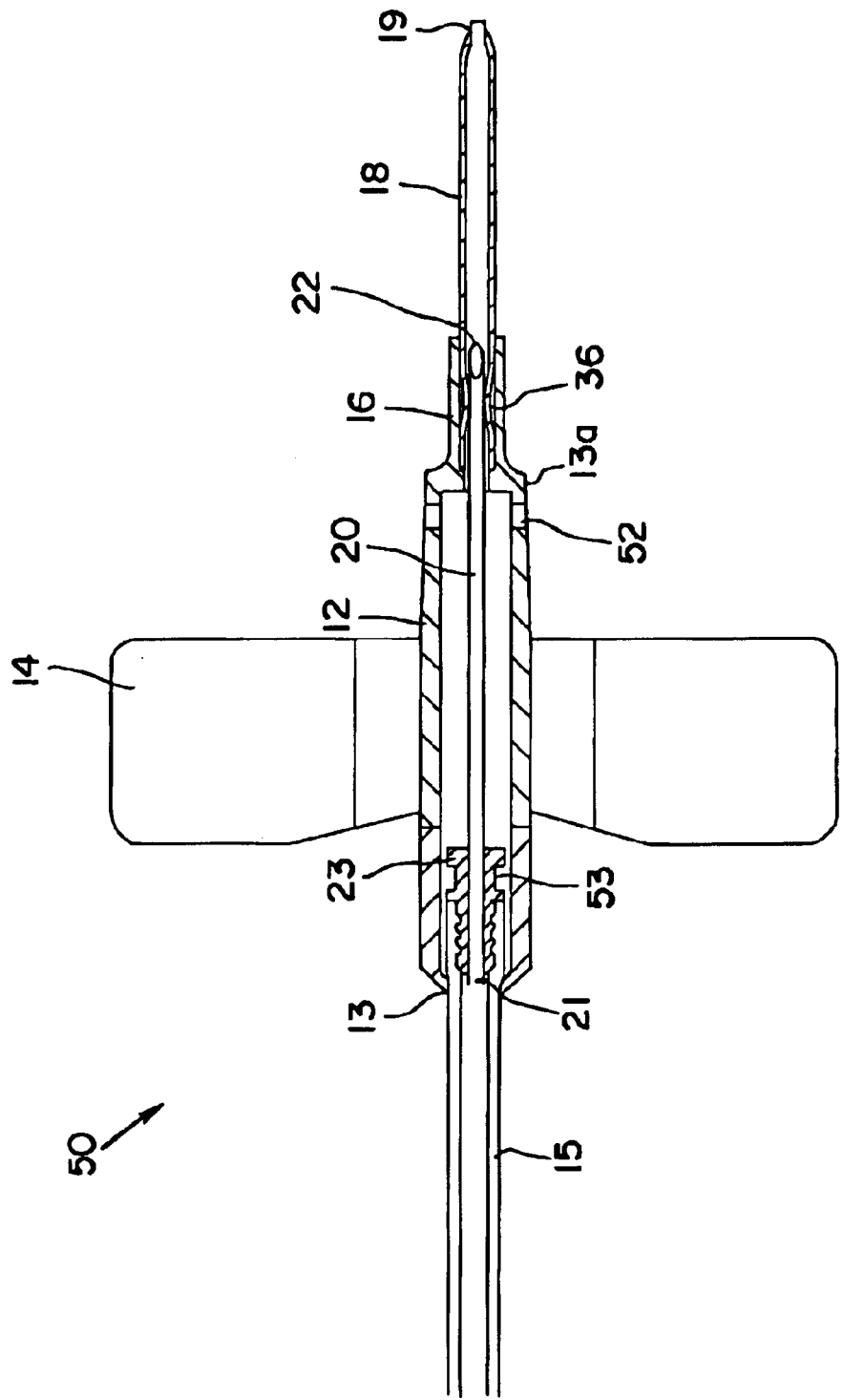
FIG. 5 is a view similar to FIG. 4 showing the parenteral catheter apparatus in a second position suitable for the prolonged transfer of parenteral fluid or for safe disposal.

FIGS. 4, 5 and 6 show a parenteral catheter apparatus 50 similar to that shown in FIGS. 1 to 3 with the addition of a plate 51 able to slide in slots 52 (see FIG. 5) through the wall of the housing 12 and with one edge cut away centrally such that the plate 51 also engages with matching grooves in sides of the hub 23. With the plate 31 in position as shown in FIG. 4 and FIG. 6, the hub 23 is fixed in position and cannot be moved axially.

In use, the needle point 22 is entered into body tissue. If desired a syringe or like device may then be fitted to the Luer or similar connector 17 and blood immediately drawn or medication delivered through the tube 15 and the needle 20. In a preferred technique, the plate 51 would first be pulled away with the finger tips and then the wings 14 would be restrained such as by applying adhesive tape to the wings and the skin, after which traction applied to the tube 15 would withdraw the needle 20 to the second position as shown in FIG. 5. Blood may then be drawn or fluid infused into a body vessel in a much more leisurely fashion, over several days if desired, limited chiefly by the sterility and properties of inner fluid path walls, especially those of the catheter 18 and the needle 20, which should preferably be coated with a surface which prevents the various forms of activation of the blood.

Figures 7, 9:
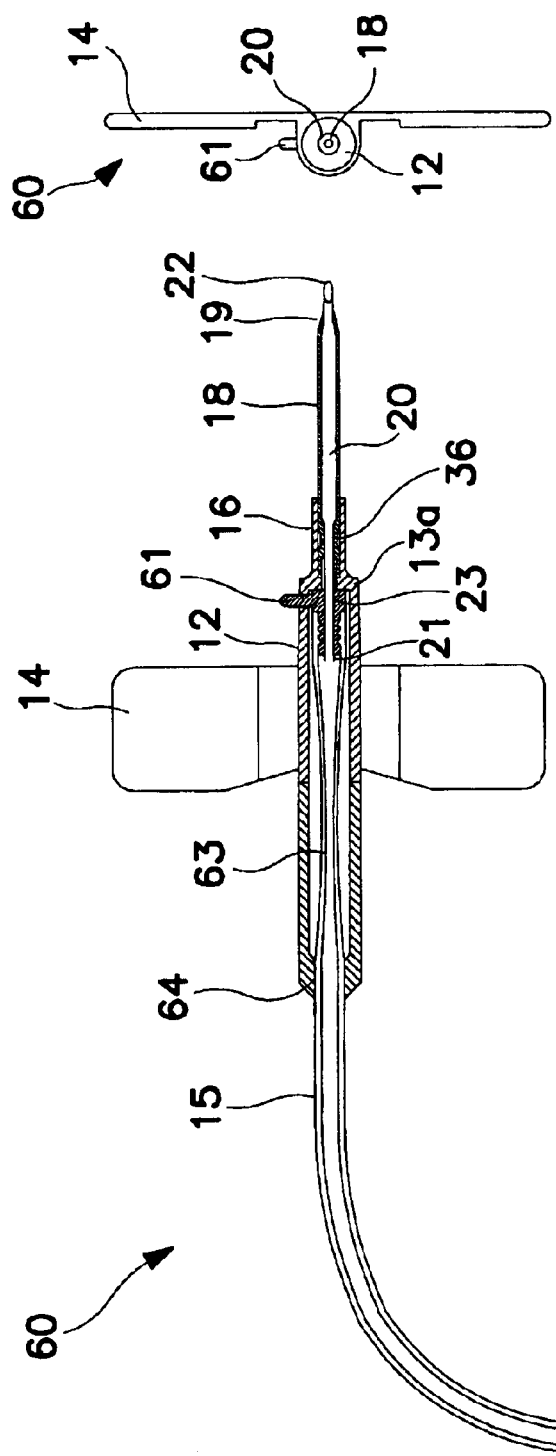
FIG. 7 is a longitudinal sectional view of a third embodiment of the parenteral catheter apparatus of the present invention with a needle apparatus in a first position ready to enter living tissue or to perform a brief injection.
FIG. 9 is a transverse view of the parenteral catheter apparatus of FIGS. 7 and 8.
Figure 8:
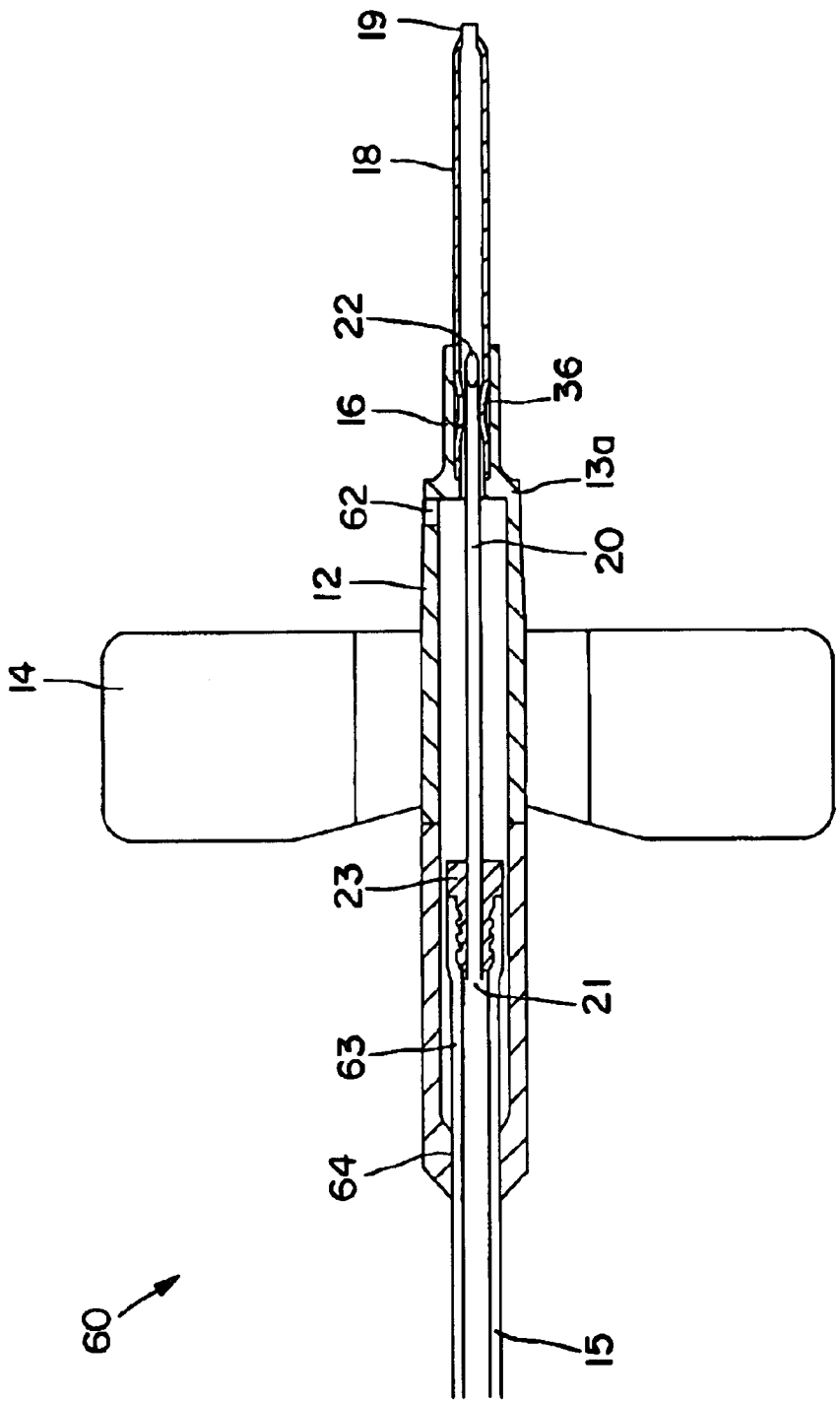
FIG. 8 is a view similar to FIG. 7 in which the parenteral catheter apparatus is in a second position suitable for the prolonged transfer of parenteral fluid or for disposal after use.

FIGS. 7, 8 and 9 illustrate a parenteral catheter apparatus 60 again similar in action to those shown in FIGS. 1 to 6 but in this embodiment a tab 61 is formed on the hub 23 and the tube 15 is firmly fixed, such as by glue or by force fit of mating flange and groove, to a second end 64 of housing 12. The tab 61 engages in the position shown in FIG. 7 with a slot 62 (see FIG. 8). Further, the tube 15 has a stretched elastic portion 63 between the end 64 and the hub 23. The tab 61 extends through an L-shaped slot formed through a wall of the housing 12. A transverse short portion of the L-shaped slot retains the hub 23 against a traction force exerted axially by an elastic portion 63 of the parenteral fluid tube 15. When it is desired to move the needle 20 from a first to a second position (see FIG. 8) the tab 61 is moved by finger pressure along the transverse arm of the L-shaped slot, allowing the tab 61 to enter an axial long arm of the L-shaped slot, so allowing the force of the tension in the stretched elastic portion 63 to move the needle apparatus to the second position shown in FIG. 8. If desired, fluid transfer may continue during this maneuver.

Figure 11:
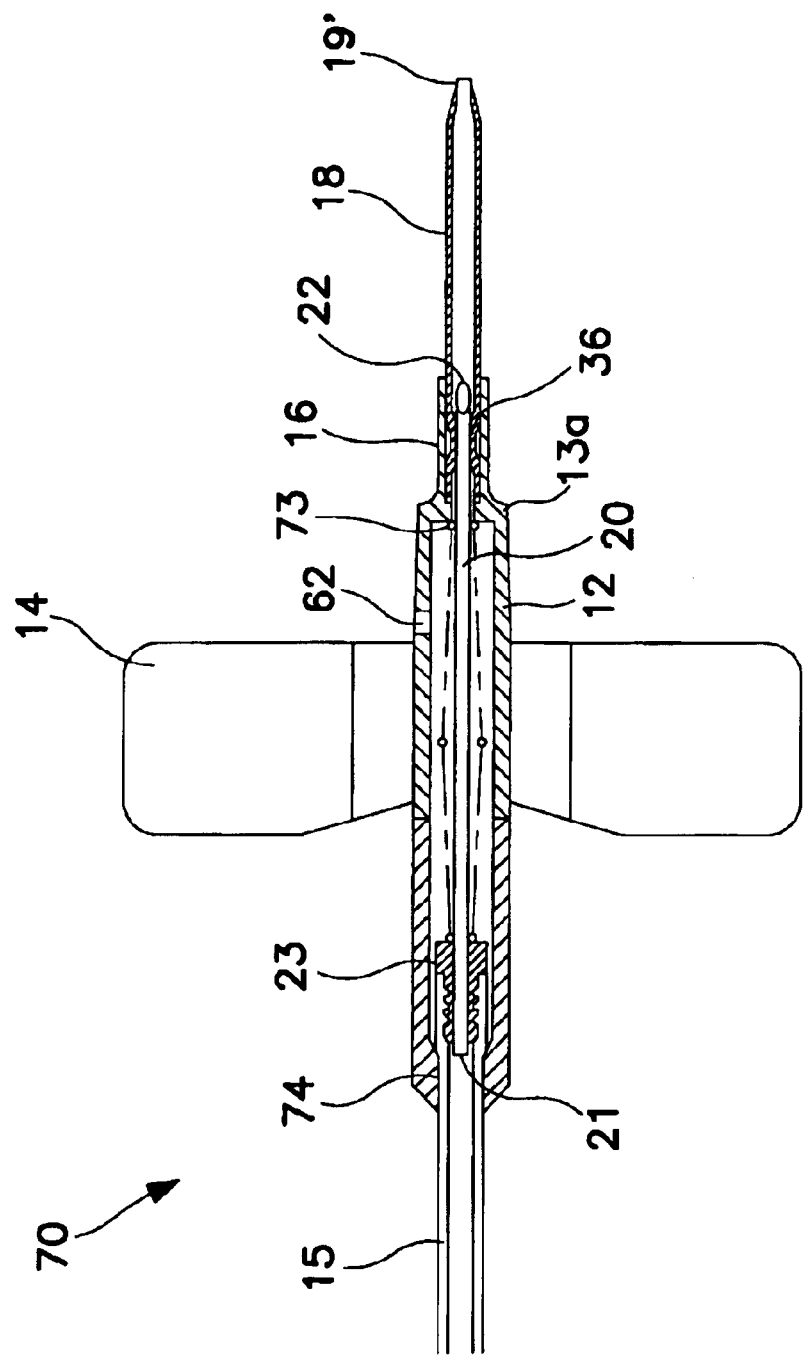
FIG. 11 is a view similar to FIG. 10 in which the parenteral catheter apparatus is in a second position.

FIG. 10, 11 and 12 illustrate a parenteral catheter apparatus 70 which is similar in construction and operation to that illustrated in FIGS. 7 to 9. In this embodiment the tube 15 runs freely through a second end 74 of the housing 12. The hub 23 has a tab 61 attached or formed thereon which passes through a slot in a wall of the housing 12. The slot is generally axially oriented but may have a transverse detente at each end for the purpose of stabilising the needle apparatus in a first or second position. A coil spring 73 is compressed between the hub 23 and an inner end of the housing 12 adjacent the tubular boss 16. Movement of the tab 61 into the axially oriented part of the slot in the housing 12 allows the needle apparatus to move from a first position shown in FIG. 10 to a second position shown in FIG. 11. If desired, transfer of parenteral fluid may continue during this manoeuvre.

Figure 14:
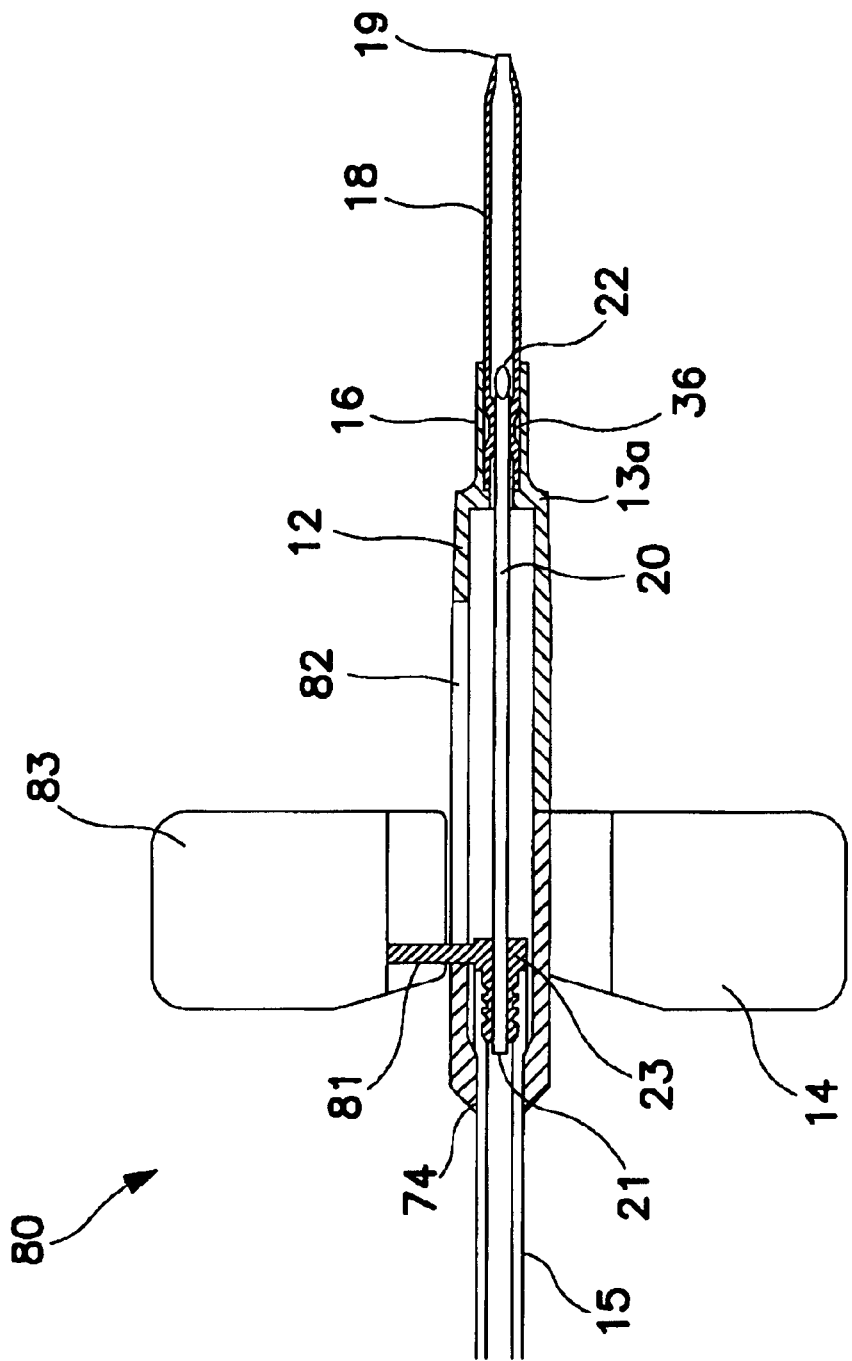
FIG. 14 is a view similar to that shown in FIG. 13 showing the fifth embodiment of parenteral catheter apparatus in a second position.

FIGS. 13, 14 and 15 illustrate a parenteral catheter apparatus 80, the structure and operation of which is generally similar to the parenteral catheter assemblies shown in FIGS. 1 to 12, the main difference being that the needle apparatus may be moved from a first to a second position by moving a wing-shaped tab 83 by finger pressure. The wing-shaped tab 83 is fixed to the hub 23 by means of an extension 81 formed on the hub 23 and passing through a slot 82 in a wall of the housing 12. In FIG. 13, the wing 83 is shown to be in the same plane as the wing 14 when in a first position. It may be more convenient however, for the extension 81 to pass through an L-shaped slot in a wall of the housing 12 arranged such that the wing 83 is substantially perpendicular to the wing 14 when in the first position. The L-shaped slot has a transverse short arm and an axial long arm. This is substantially perpendicular to the position shown in FIG. 13.

When the needle end 22 and the catheter end 19 are in the desired position in a blood vessel, the wing 83 may be rotated so that the extension 81 enters the axial long arm of the L-shaped slot. This allows the wing 83, together with the needle apparatus to be moved to a second position shown in FIG. 14. A second transverse extension at the other end of the slot would allow the wing 83 to be rotated and locked into a second position in which the wing 83 was flat and in the same plane as the wing 14. In this second position of this preferred embodiment, the wings 14 and 83 may be taped to the skin for further parenteral fluid transfer. In this position also the removed and used device may be handled and disposed of safely. It should be noted in particular that during insertion of the device into the tissue, a bevel of the end 22 is generally preferred to be up and facing the operator. In this preferred embodiment, this position would be obtained with the wing 83 in the substantially perpendicular position projecting upward from the plane of the skin. In moving to the second position the orientation of the bevel would change. In other embodiments of the parenteral catheter apparatus in accordance with the present invention the orientation of the bevel is of no consequence when in the second position.

Figure 17:
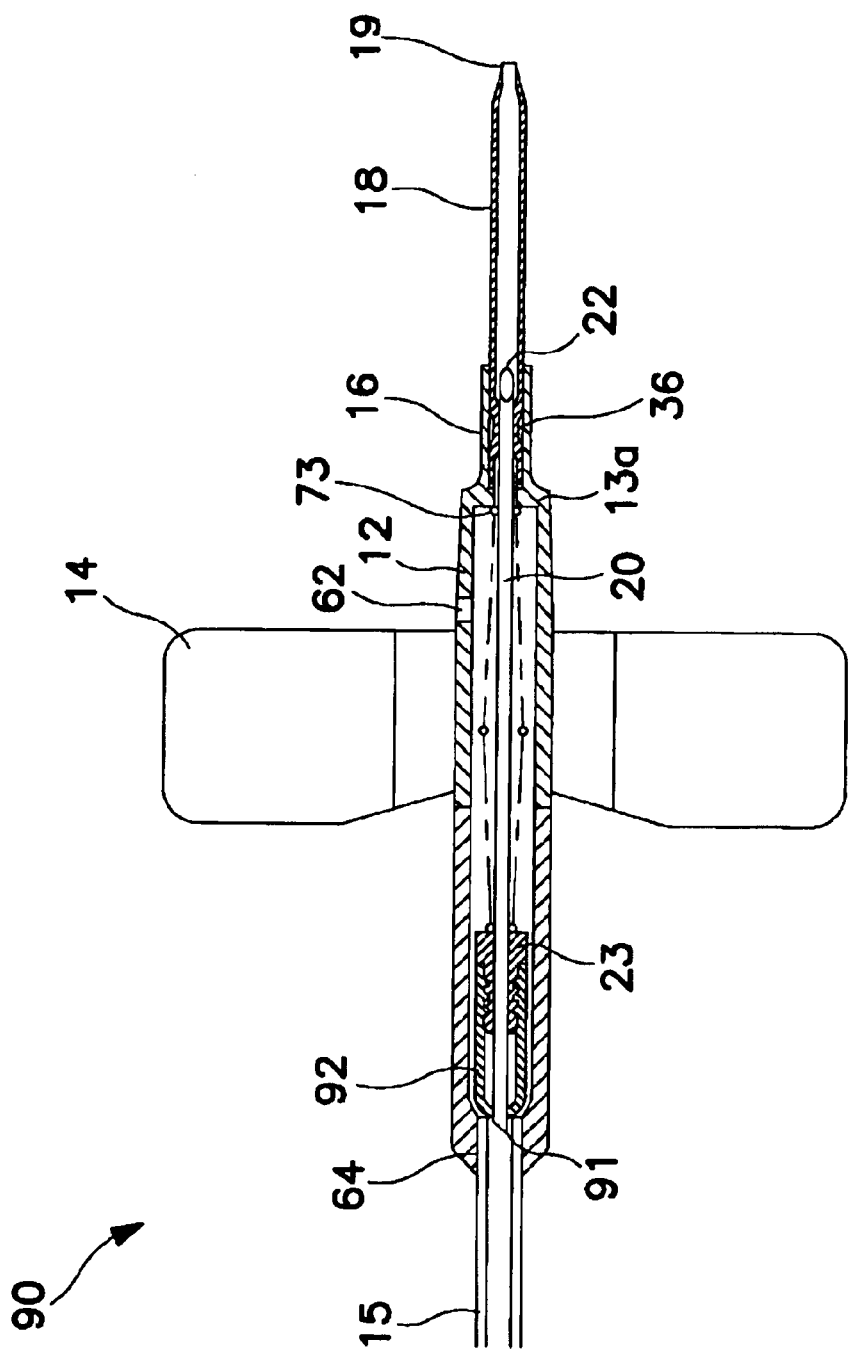
FIG. 17 is a longitudinal sectional view of the sixth embodiment of the parenteral catheter apparatus of FIG. 16 with the needle apparatus in a second position.

FIGS. 16 to 18 illustrate an embodiment of a parenteral catheter apparatus 90 in which an open fluid path is only achieved when the apparatus is in second position. In this embodiment, the needle 20 has a sharpened inner end 91 which is covered with a flexible and piercable elastomer cap 92. The cap 92 is fixed sealingly to the outside of the hub 23. Various methods of moving the needle apparatus from the first to the second position may be used, but in a preferred arrangement, the movement is achieved by the urging of a coil spring 73 in a manner similar to that shown in FIG. 11 and FIG. 12. In this embodiment the hub 23 is not attached to the tube 15 but an end of the tube 15 is fixed sealingly to the constricted end 64 of the housing 12. When the needle 20, the hub 23, the tab 61 and the cap 92 move from a first position to a second position as shown in FIG. 17, the cap 92 is driven against the adjacent end of the tube 15 and against the constricted end 64 of the housing 12. In this position the cap 92 forms a seal with the adjacent end of the tube 15 or with the housing 64. Under further urging by the spring 73, aided by momentum generated on initiation of the movement, the sharpened end 91 of the needle 20 is driven through the cap 92, so opening a fluid channel from the catheter tip 19 through the needle 20 and the tube 15. It will be noted that upon entry of the needle tip 22 into a blood vessel, blood is likely to flow into the small chamber formed by the sealing of the cap 91 to the hub 23. This provides the desired "flashback" which informs the operator that entry into a blood vessel has been successful. In a further preferred embodiment the travel of the tab 61 may be limited by slot arrangements, for example an E-shaped slot, such that there is provided a stable first position, a stable second position and a stable intermediate position, In the intermediate position the tip 22 would be located some distance back from the opening 19 of the catheter 18. The consequence of this in the embodiment as described here is a switchable catheter system, provided only that the cap 92 tends to self-seal after puncture by the end 91. This embodiment may have special advantages in many clinical situations, for example drawing blood from blood donors, where it is desirable to shut off flow to the collection bag before or after removal of the catheter from the vein of the blood donor. This would also apply to giving blood such as in emergencies and giving parenteral fluid where it may be desirable to shut off flow promptly and easily e.g. in the case of an adverse reaction to the fluid. Also, the cap 92 could be precut by means of a slit and normally closed and the needle 20 could have a blunt inner end able to pass through the slit. Further, if the needle 20 is withdrawn the slit would self seal again.

In a further preferred variation of a parenteral catheter apparatus according to the present invention the arrangement is similar to that shown in FIG. 16 but the needle 20 and the catheter 18 are of relatively large diameter, for example 14 gauge such as is used for in collecting blood from blood donors. The spring 73 may be omitted or may be a small weak spring just sufficient to overcome static friction. When the needle end 22 and the catheter end 19 are caused to enter the vein of a donor the pressure of blood in the vein, typically 70 mm Hg, due to the compression of the donor's arm by a sphygmomanometer cuff, acts on the needle 20 which is closed by the cap 92. This causes the needle 20 to move like a piston within the catheter 18 so that the needle 20 moves from the first position shown in FIG. 16 to the second position shown in FIG. 17, when the sharpened end 91 pierces the cap 92 allowing blood to flow from the vein into a receptacle connected to the tube 15.

Further, it is envisaged that the needle 20 may be provided with a shape memory alloy extension which in a cool state engages a detente or notch on an inner surface of the housing 12 but when heated to near body heat eg 30°–35° C., changes shape so that the needle is either retracted slightly. Alternatively, the extension may disengage from the detente so that the needle 20 may be moved back by urging of a spring or another elastic element. Preferably, the shape memory alloy extension is in good thermal contact with the needle 20 or the parenteral fluid so that the extension rapidly reaches about the same temperature as the needle 20.

The present invention describes how a tubular needle may be used to introduce a soft catheter into the living tissue and be then moved into a safe position in which it remains part of the parenteral fluid transfer path. The fluid transfer path remains closed to the external environment so maintaining sterility. The sharp needle end 22 can be covered during operation of the apparatus of the present invention to transfer parenteral fluid. When the operation is completed the parenteral catheter apparatus may be removed from the living body and conveyed to a suitable waste disposal container without exposing other persons to the contaminated sharp needle end 22, which during and after use is enclosed within the apparatus.

Modifications and variations such as would be apparent to a skilled addressee are deemed to be within the scope of the present invention. For example, it is envisaged that the catheter could be moveable relative to the remainder of the apparatus whilst the needle remain stationary relative to the rest of the apparatus.

Further, it is envisaged that the hub 23 could be formed in a non-circular cross sectional shape such as a square shape to prevent the hub 23 from rotating in the housing 12 so that the orientation of the needle 20 may be readily determined prior to a procedure.

What is claimed is:

1. A parenteral catheter apparatus characterised in that it comprises a thin walled catheter having a free end, the catheter closely enclosing a tubular needle having a sharp point, the catheter being mounted to a housing having a first end and a second end, the needle and catheter being longitudinally moveable relative to one another between a first position at which the needle extends from the catheter so that the sharp point is exposed and a second position at which the sharp point is within the catheter, the needle remaining in a fluid pathway of the parenteral catheter apparatus at all times between the first and second positions, the sharp point of the needle being arranged to pierce tissue when the catheter and the needle are in their relative first position, and the needle being connected or arranged to be connected to a tubular member arranged to be connected to a fluid container so that, in use, when the catheter and the needle are in their relative second position, parenteral fluid flows in order from the container into the tubular member, into the needle and into the catheter or fluid flows in the reverse direction in order into the catheter, into the needle, into the tubular member and then into the container.

2. A parenteral catheter apparatus, according to claim 1, characterised in that the housing has a forwardly projecting tubular boss adjacent the first end of the housing in which the catheter is mounted and within which the sharp point of the needle is located in the second relative position of the needle and the catheter.

3. A parenteral catheter apparatus according to claim 1 or 2, characterised in that, in the first position of the needle and the catheter, the tubular member extends through an opening in the second end of the housing and through the housing to a connection with the needle adjacent the first end of the housing.

4. A parenteral catheter apparatus according to claim 3, characterised in that the opening at the second end of the housing is constricted so as to engage with the tubular member and inhibit return of the needle to the first position.

5. A parenteral catheter apparatus according to claim 3 or 4, characterised in that latch means is provided for positively retaining the needle in the first position relative to the catheter, the latch means being moveable to enable the needle and the catheter to move axially relatively to one another.

6. A parenteral catheter apparatus according to claim 5, characterised in that the tubular member is elasticated and stretched when the needle is positively retained in the first position, such that upon the latch means being moved the tubular member contracts to move axially the needle and the catheter relative to one another.

7. A parenteral catheter apparatus according to claim 5, characterised in that spring means is mounted in the housing between the first end of the housing and the needle such that upon the latch means being moved the spring means expands to move axially the needle and the catheter relative to one another.

8. A parenteral catheter apparatus according to claim 5, characterised in that the latch means is attached to a wing shaped tab such that the latch means may be moved by the tab to enable the needle and the catheter to move axially relative to one another.

9. A parenteral catheter apparatus according to claim 8, characterised in that the tab may be used to move axially the needle and the catheter relative to one another from the first position to the second position.

10. A parenteral catheter apparatus according to claim 1 or 2, characterised in that the needle has an inner end within the housing which inner end is also sharpened, the inner end of the needle being enclosed by a sealing cap when in the first position, means being provided to move axially the needle and the catheter relative to one another so that the inner end of the needle pierces the cap, and the needle is then caused to engage sealingly with the tubular member and/or the housing so that parenteral fluid can pass from the tubular member into the needle.

11. A parenteral catheter apparatus according to claim 8 or 9, characterised in that the tab provides an indication of the orientation of a bevel at the sharp point of the needle.

* * * * *